(12) United States Patent
Mitsui et al.

(10) Patent No.: US 11,511,244 B2
(45) Date of Patent: Nov. 29, 2022

(54) FLUIDIC DEVICE, SYSTEM AND METHOD FOR DETECTING SAMPLE SUBSTANCE

(71) Applicant: NIKON CORPORATION, Tokyo (JP)

(72) Inventors: Keiji Mitsui, Kobe (JP); Ryo Kobayashi, Kawasaki (JP)

(73) Assignee: NIKON CORPORATION, Tokyo (JP)

( * ) Notice: Subject to any disclaimer, the term of this patent is extended or adjusted under 35 U.S.C. 154(b) by 1001 days.

(21) Appl. No.: 16/209,848

(22) Filed: Dec. 4, 2018

(65) Prior Publication Data

US 2019/0105618 A1 Apr. 11, 2019

Related U.S. Application Data

(63) Continuation of application No. PCT/JP2017/020792, filed on Jun. 5, 2017.

(30) Foreign Application Priority Data

Jun. 6, 2016 (JP) .............................. JP2016-112604

(51) Int. Cl.
*B01F 25/51* (2022.01)
*B01F 25/54* (2022.01)
(Continued)

(52) U.S. Cl.
CPC ............ *B01F 25/54* (2022.01); *B01F 23/451* (2022.01); *B01F 25/51* (2022.01);
(Continued)

(58) Field of Classification Search
CPC ............... G01N 1/38; G01N 2001/386; G01N 2035/00158; B01L 2300/0867; B01F 25/51; B01F 25/54
(Continued)

(56) References Cited

U.S. PATENT DOCUMENTS

| 2012/0136492 | A1 | 5/2012 | Amin et al. | |
|---|---|---|---|---|
| 2013/0260481 | A1* | 10/2013 | Shimizu | G01N 33/5302 422/69 |
| 2016/0199796 | A1* | 7/2016 | Ichiki | B01F 23/451 366/192 |

FOREIGN PATENT DOCUMENTS

| EP | 1792654 A2 | 6/2007 |
|---|---|---|
| EP | 3051293 A1 | 8/2016 |

(Continued)

OTHER PUBLICATIONS

Notice of Reasons for Refusal drafted Sep. 26, 2019 for Japanese Patent Application No. 2018-522471, with English translation, 15 pages.

(Continued)

*Primary Examiner* — Marc C Howell
(74) *Attorney, Agent, or Firm* — Squire Patton Boggs (US) LLP

(57) ABSTRACT

A fluidic device for capturing or detecting a sample substance contained in a solution includes at least two continuous circulation flow channels selected from the group consisting of: a first type continuous circulation flow channel which is formed of a first circulation flow channel and a second circulation flow channel and which is configured to circulate the solution in the first circulation flow channel and then circulate the solution in the second circulation flow channel; and a second type continuous circulation flow channel which is formed of a third circulation flow channel and a fourth circulation flow channel and which is configured to circulate the solution in the third circulation flow channel and then circulate and mix the solution in both of the third and fourth circulation flow channels, wherein any one of the circulation flow channels has a capturing section which captures the sample substance, and/or a detecting section which detects the sample substance.

20 Claims, 10 Drawing Sheets

(51) Int. Cl.

| | | |
|---|---|---|
| *C12Q 1/68* | (2018.01) | |
| *B03C 1/00* | (2006.01) | |
| *B81B 7/02* | (2006.01) | |
| *G01N 37/00* | (2006.01) | |
| *B81B 1/00* | (2006.01) | |
| *C12M 1/00* | (2006.01) | |
| *G01N 35/08* | (2006.01) | |
| *B01F 23/451* | (2022.01) | |
| *B01F 35/75* | (2022.01) | |
| *G01N 1/38* | (2006.01) | |
| *G01N 35/00* | (2006.01) | |

(52) U.S. Cl.
CPC ............ *B01F 35/7547* (2022.01); *B03C 1/00* (2013.01); *B81B 1/00* (2013.01); *B81B 7/02* (2013.01); *C12M 1/00* (2013.01); *C12Q 1/68* (2013.01); *G01N 1/38* (2013.01); *G01N 35/08* (2013.01); *G01N 37/00* (2013.01); *B01L 2300/0867* (2013.01); *G01N 2001/386* (2013.01); *G01N 2035/00158* (2013.01)

(58) Field of Classification Search
USPC ........................................................ 366/137
See application file for complete search history.

(56) References Cited

FOREIGN PATENT DOCUMENTS

| | | |
|---|---|---|
| JP | 2006-234536 A | 9/2006 |
| JP | 2007-047110 A | 2/2007 |
| JP | 2007-101428 A | 4/2007 |
| WO | WO 2010/115123 A2 | 10/2010 |
| WO | WO 2011/045288 A2 | 4/2011 |
| WO | WO 2015/046263 A1 | 4/2015 |
| WO | WO 2015/162060 A1 | 10/2015 |

OTHER PUBLICATIONS

Communication dated Nov. 15, 2019 forwarding the extended European Search Report for European Patent Application No. 17810251.3, 10 pages.
International Search Report dated Aug. 15, 2017 for PCT Application No. PCT/JP2017/020792, with English translation, 4 pages.
Written Opinion of the International Searching Authority dated Aug. 15, 2017 for PCT Application No. PCT/JP2017/020792, with English translation, 8 pages.
Hong, et al., "A nanoliter-scale nucleic acid processor with parallel architecture", Nature Biotechnology Apr. 2004, vol. 22, No. 4, pp. 435-439.

* cited by examiner

FLUIDIC DEVICE, SYSTEM AND METHOD FOR DETECTING SAMPLE SUBSTANCE

CROSS-REFERENCE TO RELATED APPLICATION

This is a Continuation Application of International Application No. PCT/JP2017/020792, filed on Jun. 5, 2017, which claims priority on Japanese Patent Application No. 2016-112604, filed on Jun. 6, 2016. The contents of the aforementioned applications are incorporated herein by reference.

BACKGROUND

Field of the Invention

The present invention relates to a fluidic device, a system, and a method for detecting a sample substance.

Background

In recent years, the development of Micro-Total Analysis Systems (µ-TAS) aiming at high-speed testing, high efficiency, and integration of testing in the field of in vitro diagnosis, or ultra-miniaturization of the testing equipment, etc., has attracted attention, and active studies are under way worldwide.

µ-TAS is superior to conventional inspection equipment in that measurement and analysis can be performed with a small amount of a sample, portability and disposability can be realized at low cost, etc.

Also, it has attracted attention as a method that is highly useful in the case of using expensive reagents or inspecting small amounts of many specimens.

As a component of µ-TAS, a device including a loop-shaped flow channel and a pump arranged on the flow channel has been reported (Jong Wook Hong, Vincent Studer, Giao Hang, W French Anderson and Stephen R Quake, Nature Biotechnology 22, 435-439 (2004)). In this device, by injecting a plurality of solutions into the loop-shaped flow channel and operating the pump, the plurality of solutions are mixed in the loop shaped flow channel.

SUMMARY

In the field of in vitro diagnosis, especially point of care testing (POCT), it is necessary to perform multiple reactions continuously and in a short time with a small amount of a sample. The µ-TAS described in Jong Wook Hong, Vincent Studer, Giao Hang, W French Anderson and Stephen R Quake, Nature Biotechnology 22, 435-439 (2004) failed to sufficiently solve this problem.

An aspect of the present invention is to provide a fluidic device which is low in cost, can easily perform an inspection procedure involving a plurality of reactions, and can shorten the inspection time.

One embodiment of the present invention provides the following (1) to (4).

(1) A fluidic device according to one embodiment of the present invention is a fluidic device for capturing or detecting a sample substance contained in a solution, which includes at least two continuous circulation flow channels selected from the group consisting of: a first type continuous circulation flow channel which is formed of a first circulation flow channel and a second circulation flow channel and which is configured to circulate the solution in the first circulation flow channel and then circulate the solution in the second circulation flow channel; and a second type continuous circulation flow channel which is formed of a third circulation flow channel and a fourth circulation flow channel and which is configured to circulate the solution in the third circulation flow channel and then circulate and mix the solution in both of the third and fourth circulation flow channels, wherein any one of the circulation flow channels has a capturing section which captures the sample substance, and/or a detecting section which detects the sample substance.

(2) A system according to one embodiment of the present invention includes the fluidic device and a control unit for controlling opening and closing of a valve.

(3) A fluidic device according to one embodiment of the present invention is a fluidic device for capturing or detecting a sample substance contained in a solution, which includes a first circulation flow channel, a second circulation flow channel, and a third circulation flow channel, wherein the first circulation flow channel and the second circulation flow channel share a first shared flow channel, the first circulation flow channel and the third circulation flow channel share a second shared flow channel, and the first shared flow channel or the second shared flow channel has a capturing section which captures the sample substance, and/or the first shared flow channel or the second shared flow channel has a detecting section which detects the sample substance.

(4) A method for detecting a sample substance according to one embodiment of the present invention includes using a fluidic device including a continuous circulation flow channel which is formed of a first circulation flow channel and a second circulation flow channel and which is configured to circulate a solution in the first circulation flow channel and then circulate and mix solutions in both circulation flow channel of the first circulation flow channel and the second circulation flow channel, and a third circulation flow channel which shares at least a portion of the flow channel with the continuous circulation flow channel and which is configured to circulate the solution after circulating the solution in the continuous circulation flow channel, the fluidic device having a capturing section for capturing a sample substance at the flow channel shared by the continuous circulation flow channel and the third circulation flow channel, and further includes the steps of: introducing a solution containing the sample substance into the first circulation flow channel of the continuous circulation flow channel; obtaining a first mixed solution by circulating and mixing the solution containing the sample substance and a pretreatment solution in the first circulation flow channel of the continuous circulation flow channel; obtaining a second mixed solution containing a complex of the sample substance and a carrier particle by circulating the first mixed solution and a solution containing the carrier particle bound to the sample substance in both of the circulation flow channels of the continuous circulation flow channel; capturing the complex in the capturing section by further circulating the second mixed solution in the continuous circulation flow channel; removing the second mixed solution from a flow channel shared by the continuous circulation flow channel and the third circulation flow channel; and detecting the sample substance by circulating a detection solution in the third circulation flow channel while releasing or not releasing the sample substance or the complex from the capturing section.

DESCRIPTION OF EMBODIMENTS

Figure 1:
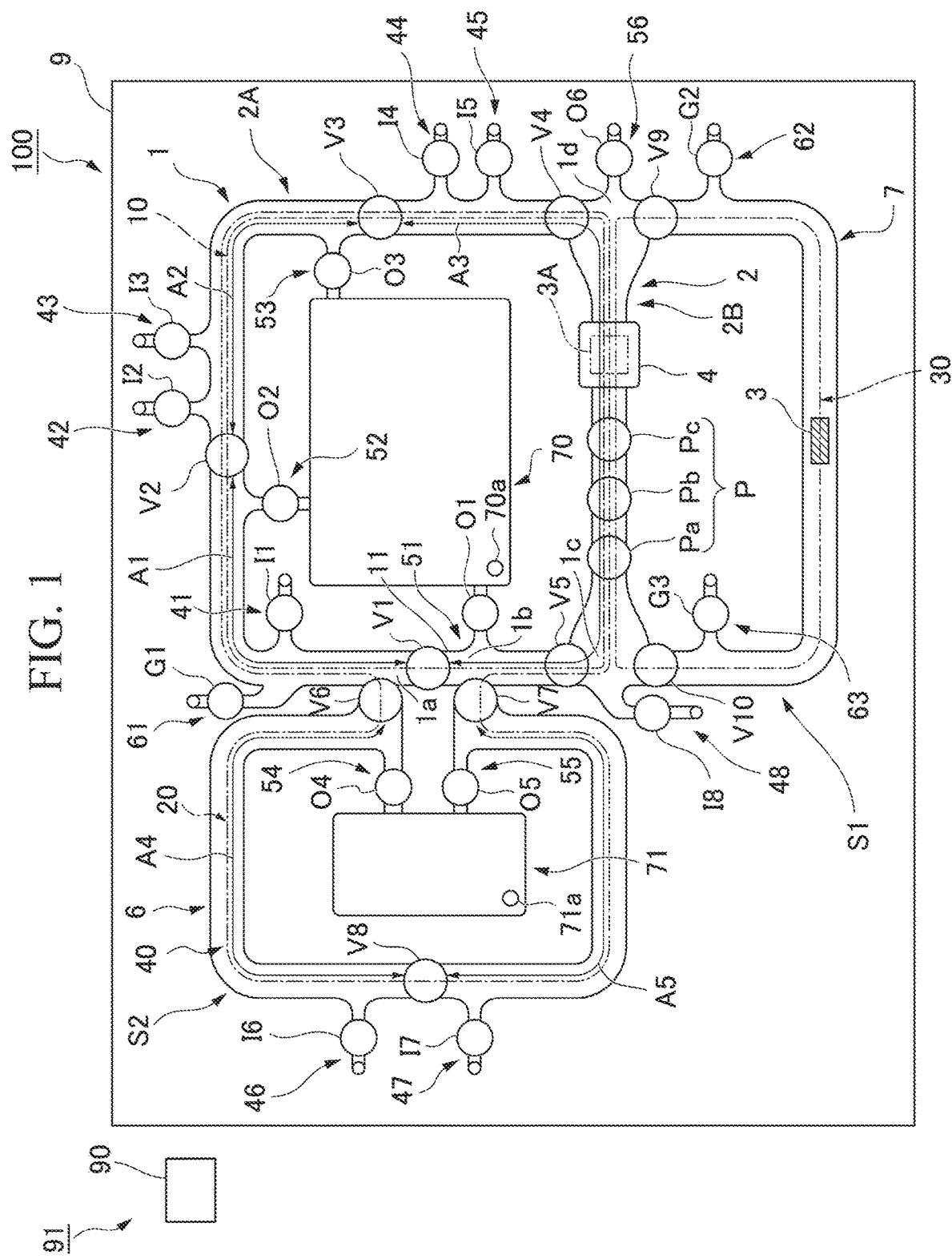
FIG. 1 is a plan view for schematically showing a fluidic device according to a first embodiment.

Hereinafter, a fluidic device according to an embodiment will be described with reference to the drawings. In the drawings used in the following description, characteristic portions may be shown in an enlarged manner for the sake of convenience to make the features easier to understand, and the dimensional proportions of the components are not necessarily the same as the actual ones.

First Embodiment

FIG. 1 is a plan view for schematically showing a fluidic device 100 of a first embodiment.

The fluidic device 100 of the present embodiment is a device for purifying and detecting a sample substance contained in a specimen sample. The sample substance is, for example, a biomolecule such as nucleic acid, DNA, RNA, a peptide, a protein, an extracellular vesicle and the like. The fluidic device 100 is provided with a substrate 9 on which a flow channel and a valve are formed.

The flow channel formed in the substrate 9 of the fluidic device 100 is divided into a loop flow channel 1 which is formed in a closed loop shape, a first bypass flow channel 6 which bypasses a pair of connection portions 1a and 1b of the loop flow channel 1, and a second bypass flow channel 7 which bypasses a pair of connection portions 1c and 1d of the loop flow channel 1. A waste liquid tank 70 is provided inside the loop flow channel 1. A waste liquid tank 71 is provided inside the first bypass flow channel 6.

The loop flow channel 1, the first bypass flow channel 6 and the second bypass flow channel 7 form a first circulation flow channel 10, a second circulation flow channel 20, a third circulation flow channel 30, and a fourth circulation flow channel 40. That is, the fluidic device 100 includes the first circulation flow channel 10, the second circulation flow channel 20, the third circulation flow channel 30, and the fourth circulation flow channel 40.

Figure 2A:
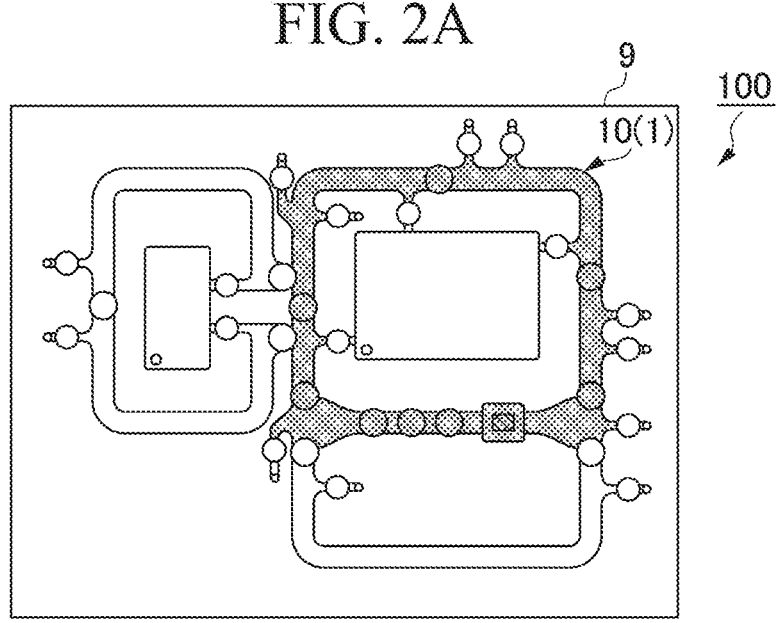
FIG. 2A is a plan view for schematically showing the fluidic device according to the first embodiment, in which a first circulation flow channel is emphasized.
Figure 2B:
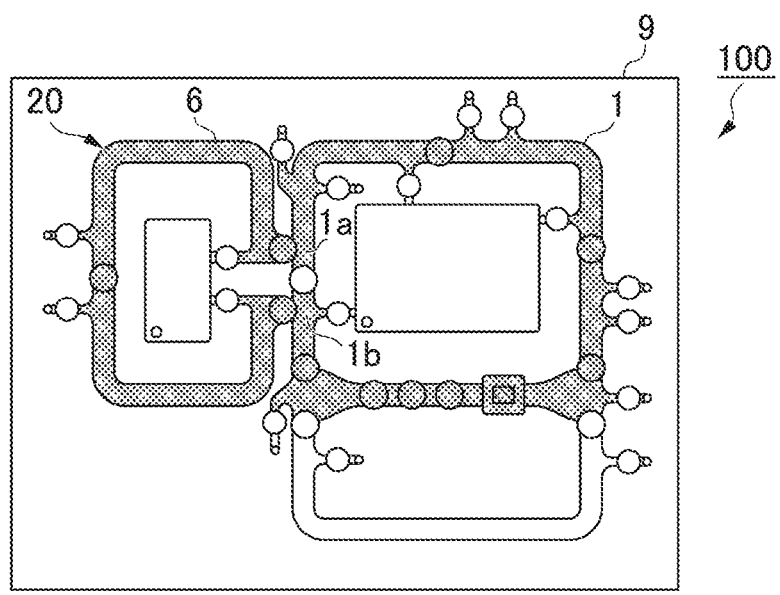
FIG. 2B is a plan view for schematically showing the fluidic device of the first embodiment, in which a second circulation flow channel is emphasized.
Figure 2C:
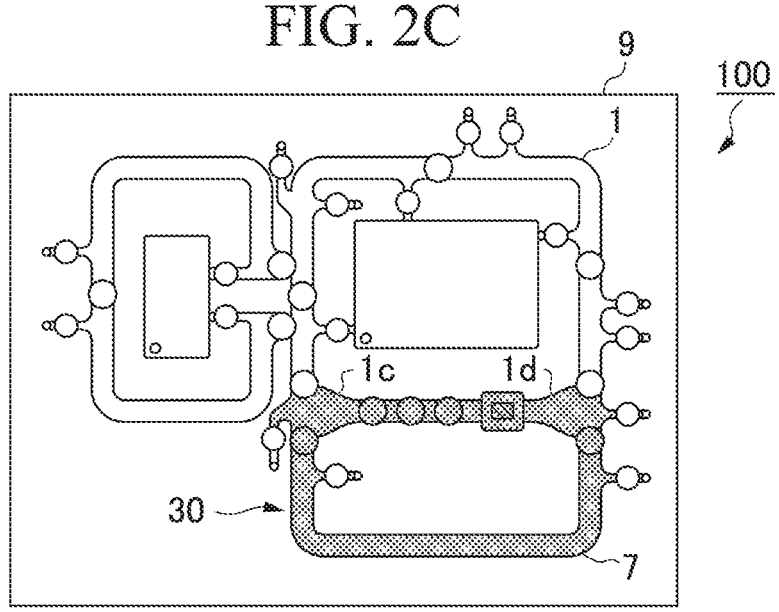
FIG. 2C is a plan view for schematically showing the fluidic device of the first embodiment, in which a third circulation flow channel is emphasized.
Figure 2D:
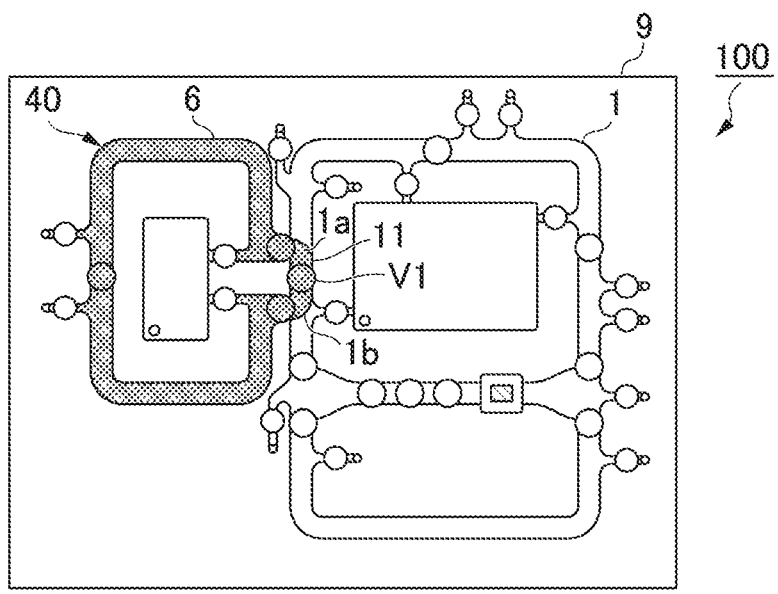
FIG. 2D is a plan view for schematically showing the fluidic device of the first embodiment, in which a fourth circulation flow channel is emphasized.

FIG. 2A shows the first circulation flow channel 10 emphasized with a dot pattern. FIG. 2B shows the second circulation flow channel 20 emphasized with a dot pattern. FIG. 2C shows the third circulation flow channel 30 emphasized with a dot pattern. FIG. 2D shows the fourth circulation flow channel 40 emphasized with a dot pattern.

As shown in FIG. 2A, the first circulation flow channel 10 is formed of the loop flow channel 1. That is, the first circulation flow channel 10 includes the entire loop flow channel 1.

As shown in FIG. 2B, the second circulation flow channel 20 is formed with a portion of the loop flow channel 1 and the first bypass flow channel 6. In the present embodiment, the portion of the loop flow channel 1 included in the second circulation flow channel 20 is one flow channel having a long distance among two flow channels divided by the pair of connection portions 1a and 1b in the loop flow channel 1.

As shown in FIG. 2C, the third circulation flow channel 30 is formed with a portion of the loop flow channel 1 and the second bypass flow channel 7. In the present embodiment, the portion of the loop flow channel 1 included in the third circulation flow channel 30 is one flow channel having a short distance among two flow channels divided by the pair of connection sections 1c and 1d in the loop flow channel 1.

As shown in FIG. 2D, the fourth circulation flow channel 40 is formed with a portion of the loop flow channel 1 and the first bypass flow channel 6. In the present embodiment, the portion of the loop flow channel 1 included in the fourth circulation flow channel 40 is a partial flow channel 11 of the loop flow channel 1 which is not included in the second circulation flow channel 20 and the third circulation flow channel 30. The partial flow channel 11 is one flow channel having a short span among the two flow channels divided by the pair of connection sections 1a and 1b to which the first bypass flow channel 6 is connected in the loop flow channel 1. The fourth circulation flow channel 40 shares the first bypass flow channel 6 with the second circulation flow channel 20. In the present embodiment, the fourth circulation flow channel 40 is not used as a single body for circulating a liquid, and is mainly used to quantify a solution. More specifically, as will be described in the description of a detection method later, the fourth circulation flow channel 40 is provided to circulate and mix solutions in both circulation flow channels of the first circulation flow channel 10 and the fourth circulation flow channel 40 after quantifying and circulating a solution in the first circulation flow channel. The first circulation flow channel 10 and the fourth circulation flow channel 40 are connected to form a second circulation flow channel 20. The valve V1 may be disposed between the connection portions 1a and 1b (the short one, that is, the partial flow channel 11) in the loop flow channel 1, and may be closed when a liquid is circulated in the second circulation flow channel 20. In this way, the liquid can flow in the second circulation flow channel in one direction.

Also, in the loop flow channel 1, by disposing valves in the vicinities of the connection portions 1*a* and 1*b* in the long one of the two flow channels divided by the connection portions 1*a* and 1*b* and closing these valves, the fourth circulation flow channel 40 may be configured as a single body to circulate the liquid.

The first circulation flow channel 10 and the fourth circulation flow channel 40 form a second continuous circulation flow channel (a second type continuous circulation flow channel) S2. The second circulation flow channel 20 and the third circulation flow channel 30 have a shared flow channel (a second shared flow channel 2B). The second circulation flow channel 20 and the third circulation flow channel 30 are configured to be able to circulate a solution in the third circulation flow channel 30 after the circulating the solution in the second circulation flow channel 20. The second circulation flow channel 20 and the third circulation flow channel 30 form a first continuous circulation flow channel (a first type continuous circulation flow channel) S1.

The first circulation flow channel 10 and the second circulation flow channel 20 have a first shared flow channel 2A shared with each other.

The first circulation flow channel 10 and the third circulation flow channel 30 have a shared flow channel (the second shared flow channel 2B). The first shared flow channel 2A and the second shared flow channel 2B share at least a portion of the flow channels (an overlapping shared flow channel 2). In the present embodiment, the entire length of the second shared flow channel 2B overlaps the entire length of the overlapping shared flow channel 2.

A continuous circulation flow channel is divided into the first type continuous circulation flow channel and the second type continuous circulation flow channel. The first type continuous circulation flow channel is formed with two circulation flow channels and is configured to be able to circulate a solution in one circulation flow channel and then circulate the solution in the other circulation flow channel. Also, the second type continuous circulation flow channel is formed with two circulation flow channels and is configured to be able to circulate a solution in one circulation flow channel and then circulate and mix solutions in both circulation flow channels. In addition, the other flow channel in the second type continuous circulation flow channel may be sufficient as long as it can circulate both the liquid contained therein and the liquid contained in the one circulation flow channel together, and may not be configured to circulate a liquid independently.

The fluidic device of the present embodiment includes at least two continuous circulation flow channels selected from the group consisting of the first type continuous circulation flow channel and the second kind continuous circulation flow channel. Therefore, when the fluidic device of the present embodiment includes two continuous circulation flow channels, it may be any one of one including two first type continuous circulation flow channels, one including two second type continuous circulation flow channels, and one including each of the first type continuous circulation flow channel and the second type continuous circulation flow channel. When the fluidic device of the present embodiment includes three or more continuous circulation flow channels, all of them may be the first type continuous circulation flow channels or the second type continuous circulation flow channels, or they may include both of the first type and second type continuous circulation flow channels.

In the fluidic device of the present embodiment, two or more continuous circulation flow channels may share a circulation flow channel. For example, when the fluidic device of the present embodiment includes the first type continuous circulation flow channel and the second type continuous circulation flow channel, one circulation flow channel of the first type continuous circulation flow channel may be used as one circulation flow channel of the second type continuous circulation flow channel.

The first continuous circulation flow channel S1 is formed of two circulation flow channels (the second circulation flow channel 20 and the third circulation flow channel 30). Further, the first continuous circulation flow channel S1 is configured to circulate a solution in one circulation flow channel (the second circulation flow channel 20) and then circulate the solution in the other circulation flow channel (the third circulation flow channel 30). Therefore, the first continuous circulation flow channel S1 is classified as the first type continuous circulation flow channel. The two circulation flow channels (the second circulation flow channel 20 and the third circulation flow channel 30) in the first continuous circulation flow channel S1 share a portion of the flow channels (the second shared flow channel 2B).

The second continuous circulation flow channel S2 is formed of two circulation flow channels (the first circulation flow channel 10 and the fourth circulation flow channel 40). The second continuous circulation flow channel S2 is configured to circulate a solution in one circulation flow channel (the first circulation flow channel 10), and then circulate and mix solutions in both circulation flow channels (that is, the second circulation flow channel 20) of the first circulation flow channel 10 and the fourth circulation flow channel 40. Therefore, the second continuous circulation flow channel S2 is classified as the second type continuous circulation flow channel.

(First Circulation Flow Channel)

The first circulation flow channel 10 is provided with a plurality of valves V1, V2, V3, V4 and V5. Among the plurality of valves V1, V2, V3, V4 and V5, the valves V1, V2 and V3 function as quantitative valves, and the valves V4 and V5 function as shared flow channel terminal valves which partition the overlapping shared flow channel 2 from other areas.

Further, in the overlapping shared flow channel 2 of the first circulation flow channel 10, a capturing section 4 and a pump P are disposed.

The quantitative valves V1, V2 and V3 divide the first circulation flow channel 10 into a first quantitative section A1, a second quantitative section A2, and a third quantitative section A3. That is, the quantitative valves V1, V2 and V3 are arranged such that each of the sections of the first circulation flow channel 10 delimited by the quantitative valves has a predetermined volume. More specifically, the first quantitative section A1 is formed between the quantitative valves V1 and V2. The second quantitative section A2 is formed between the quantitative valves V2 and V3. The third quantitative section A3 is formed between the quantitative valves V1 and V3.

An introduction flow channel 41, a discharge flow channel 52, and an air flow channel 61 are connected to the first quantitative section A1 of the first circulation flow channel 10. Introduction flow channels 42 and 43 and a discharge flow channel 53 are connected to the second quantitative section A2. Introduction flow channels 44, 45 and 48, a discharge flow channel 51, and a discharge flow channel (a recovery flow channel) 56 are connected to the third quantitative section A3. In particular, the introduction flow channel 48 and the discharge flow channel 56 are disposed at both ends of the overlapping shared flow channel 2 in the third quantitative section A3.

The shared flow channel terminal valves V4 and V5 partition the first circulation flow channel 10 into the overlapping shared flow channel 2 and other areas. The shared flow channel terminal valves V4 and V5 are positioned at both ends of the overlapping shared flow channel 2 in the first circulation flow channel 10. The shared flow channel terminal valves V4 and V5 are positioned together in the third quantitative section A3. The entire area of the overlapping shared flow channel 2 is included in the third quantitative section A 3 of the first circulation flow channel 10.

(Second Circulation Flow Channel)

The second circulation flow channel 20 has the first shared flow channel 2A which is shared with the first circulation flow channel 10, and the first bypass flow channel 6 which is not shared with the first circulation flow channel 10.

In the first shared flow channel 2A, the plurality of valves V1, V2, V3, V4 and V5 described above are provided. In addition, a portion of the first shared flow channel 2A overlaps the overlapping shared flow channel 2. Therefore, the first shared flow channel 2A has the capturing section 4 and the pump P. The introduction flow channels 41, 42, 43, 44, 45 and 48, the discharge flow channels 51, 52, 53 and 56 and the air flow channel 61 are connected to the first shared flow channel 2A.

The first bypass flow channel 6 is provided with a plurality of valves V6, V7 and V8. Among the plurality of valves V6, V7 and V8, the valves V6 and V7 are positioned at terminals of the first bypass flow channel 6 and function as first bypass flow channel terminal valves which partition the first bypass flow channel 6 and the first shared flow channel 2A. In addition, the valve V8 functions as a quantitative valve. The quantitative valve V8 partitions the first bypass flow channel 6 into two regions of a predetermined volume. In the first bypass flow channel 6, a fourth quantitative section A4 is formed between the quantitative valve V8 and the first bypass flow channel terminal valve V6. In the first bypass flow channel 6, a fifth quantitative section A5 is formed between the quantitative valve V8 and the first bypass flow channel terminal valve V7. An introduction flow channel 46 and a discharge flow channel 54 are connected to the vicinities of both ends of the fourth quantitative section A4. Similarly, an introduction flow channel 47 and a discharge flow channel 55 are connected to the vicinities of both ends of the fifth quantitative section A5.

(Third Circulation Flow Channel)

The third circulation flow channel 30 has a second shared flow channel 2B shared with the first circulation flow channel 10 and the second bypass flow channel 7 not shared with the first circulation flow channel 10.

As described above, the entire area of the second shared flow channel 2B coincides with the overlapping shared flow channel 2. Therefore, the capturing section 4 and the pump P are disposed in the second shared flow channel 2B. Also, valves V9 and V10 are provided at both ends of the second shared flow channel 2B in the third circulation flow channel 30. The valves V9 and V10 function as shared flow channel terminal valves. That is, the shared flow channel terminal valves V9 and V10 partition the third circulation flow channel 30 into the second shared flow channel 2B and the second bypass flow channel 7.

Air flow channels 62 and 63 are connected to the vicinities of both ends of the second bypass flow channel 7. A detecting section 3 is provided in the second bypass flow channel 7.

Each component provided in the flow channels will be described in detail below.

(Pump)

The pump P is formed of three pump valves Pa, Pb, and Pc arranged side by side in the flow channel. The pump P can convey the liquid in the circulation flow channel by sequentially opening and closing the three pump valves Pa, Pb, and Pc. The number of valves constituting the pump valve may be 4 or more.

The pump P circulates the liquid in the first circulation flow channel 10, the second circulation flow channel 20, and the third circulation flow channel 30. The flow velocity of the liquid circulating in the first circulation flow channel 10, the second circulation flow channel 20, and the third circulation flow channel 30 becomes slow near the wall surface of the flow channels due to the interaction (friction) between the wall surface of the flow channels and the solution in the flow channels and becomes faster in the center of the flow channels. As a result, distribution of the liquid flow velocity is generated, so that mixing of the solution is promoted. That is, driving the pump P creates convection in the liquid in the first circulation flow channel 10, so that mixing of a plurality of liquids is promoted.

(Capturing Section)

The capturing section 4 captures and collects the sample substance in the solution circulating in the first circulation flow channel 10.

Also, the capturing section 4 may capture carrier particles bound to the sample substance. By capturing the sample substance itself or carrier particles bound to the sample substance, the capturing section 4 can recover the sample substance from the liquid circulating in the first circulation flow channel 10. The fluidic device 100 can effectively concentrate, wash, and transport sample substances when the capturing section 4 is provided.

In the capturing section 4 of the present embodiment, for example, a magnetic force generation source such as a magnet or the like can be disposed in the vicinity thereof. In that case, if magnetic beads or magnetic particles are used as carrier particles, the carrier particles can be captured due to the magnetic force. In other examples of the capturing section 4, a column having a filler capable of binding to carrier particles, an electrode capable of attracting carrier particles, etc., may be included. Further, when the sample substance is a nucleic acid, the capturing section 4 may be a nucleic acid array in which nucleic acids hybridizing with the nucleic acid are immobilized. When the sample substance is an antigen, an antibody array in which an antibody against the antigen is immobilized may be used.

Carrier particles are, for example, particles that can react with the sample substance. The reaction between the carrier particles and the sample substance can be exemplified by, for example, a combination of a carrier particle and a sample substance, adsorption between a carrier particle and a sample substance, a modification of a carrier particle by a sample substance, a chemical change of a carrier particle by a sample substance, etc.

In examples of the carrier particles, magnetic beads, magnetic particles, gold nanoparticles, agarose beads, plastic beads, etc., may be included.

For binding carrier particles and the sample substance, carrier particles having, on the surface thereof, a substance capable of binding or adsorbing to the sample substance may be used. For example, when binding a carrier particle and a protein, by using a carrier particle having on its surface an antibody capable of binding to the protein, it is possible to bind the antibody on the surface of the carrier particle and the protein. The substance capable of binding to the sample substance may be appropriately selected according to the type of the sample substance. As an example of a combination of a substance capable of binding to or adsorbing to a sample substance/the sample substance or a site included in the sample substance, a biotin-binding protein/biotin such as avidin and streptavidin, an active ester group such as a succinimidyl group/amino group, an acetyl iodide group/amino group, a maleimide group/thiol group (—SH), a maltose-binding protein/maltose, a G protein/guanine nucleotide, polyhistidine peptide/metal ions of nickel, cobalt, or the like, glutathione-S-transferase/glutathione, a DNA-binding protein/DNA, an antibody/antigen molecule (epitope), calmodulin/a calmodulin-binding peptide, an ATP-binding protein/ATP, or various receptor protein/ligands thereof such as an estradiol receptor protein/estradiol or the like can be exemplified.

The carrier particles and the sample substance may react in the first circulation flow channel 10. For example, by introducing the liquid containing the carrier particles and the sample substance into the first circulation flow channel 10 and circulating and mixing them in the circulation flow channel, a complex in which the carrier particles and the sample substance are combined is formed. For example, when a biological molecule is immobilized on a surface of the particles and there is a sample substance that binds to the biological molecule on the surface of the particle in the liquid, mixing makes it possible to increase the collision frequency to improve the coupling reaction speed between them. This technique is suitable, for example, for immunoassays in which measurement of single items is common.

The magnetic force of the capturing section 4 can preferably be controllable. Capture and release of the carrier particles can be controlled by controlling the magnetic force of the magnetic force generation source applied to the carrier particles. That is, the capturing section 4 is configured to be able to control the affinity for carrier particles. For example, the capturing section 4 may control the magnetic force applied to the carrier particles by changing the distance between the magnet and the circulation type flow channel. When the carrier particles become free from the captured state, the carrier particles are dispersed in the solution again. In the case of using an electromagnet as the capturing section 4, the magnetic force may be controlled by ON/OFF of the current and control of the current value to capture and release the carrier particles by the capturing section 4.

The capturing section 4 may be an array in which carrier particles can be arranged. As such a form, one in which regions capable of capturing carrier particles are arranged in an array, one in which holes capable of containing carrier particles are arranged in an array, and the like can be exemplified. For example, the region where the carrier particles can be captured may be well-shaped. The size of the wells may be 1 to 2 times the diameter of the carrier particles so that the carrier particles are contained one by one. Further, a capturing means may be a magnet array in which a plurality of magnets are arranged in an array. In the capturing section 4, a sample substance binding to carrier particles may be analyzed with the carrier particles captured. By arraying and capturing the carrier particles, the analysis of the sample substance binding to the carrier particles becomes more efficient.

(Detecting Section)

The detecting section 3 is provided for detecting a sample substance. The term "detecting a sample substance" is used in a sense that also includes indirectly detecting a sample substance. As an example of indirectly detecting a sample substance, the sample substance may be combined with a detection assisting substance that assists with the detection of the sample substance. As the detection assisting substance, a labeling substance can be used.

As the labeling substance (detection assisting substance), for example, fluorescent dyes, fluorescent beads, fluorescent proteins, quantum dots, gold nanoparticles, biotin, antibodies, antigens, energy absorbing substances, radioisotopes, chemiluminescent substances, enzymes, and the like can be employed.

As the fluorescent dyes, carboxyfluorescein (FAM), 6-carboxy-4',5'-dicloro2',7'-dimethoxyfluorescein (JOE), fluorescein isothiocyanate (FITC), tetrachlorofluorescein (TET), 5'-hexachloro-fluorescein-CEphosphoroamidite (HEX), Cy3, Cy5, Alexa568, Alexa647, and the like can be employed.

As the enzymes, alkaline phosphatase, peroxidase, and the like can be employed.

The detecting section 3 can detect the sample substance by detecting the labeling substance mentioned above. The detecting section 3 may optically detect the sample substance, and can have a configuration, for example, in which an object lens or an imaging unit can be disposed in the vicinity thereof. The imaging unit may have, for example, an electron multiplying charge coupled device (EMCCD) camera. Also, the detecting section 3 may electrochemically detect the sample substance, and can have a configuration, for example, in which an electrode can be disposed in the vicinity thereof.

The detecting section 3 may be provided together with the capturing section 4 capable of capturing the sample substance. By arranging the detecting section 3 toward the capturing section 4, the sample substance captured by the capturing section 4 can be efficiently detected.

(Introduction Flow Channels)

The introduction flow channels 41 to 48 are provided for introducing different liquids into the first circulation flow channel 10, the second circulation flow channel 20, or the third circulation flow channel 30. The introduction flow channels 41 to 48 are provided with introduction flow channel valves I1 to I8 for opening and closing the introduction flow channels, respectively. Also, at ends of the introduction flow channels 41 to 48, liquid introduction inlets which are opened on a surface of the substrate 9 are provided.

The introduction flow channels 41 to 48 are disposed in the vicinities of the valves (the quantitative valves) for partitioning the regions into which the liquid is introduced. When the liquid is introduced from the introduction flow channels 41 to 48 with the quantitative section empty (filled with air), the air in the flow channel is pushed out by the liquid and the air is discharged from the air flow channel which is not shown. At this time, if the quantitative valve and the introduction flow channel are separated from each other, the air between the quantitative valve and the introduction flow channel is not discharged and air pockets are easily generated, and therefore, there is a possibility that the liquid will not fill up to the quantitative valve. By placing the introduction flow channels 41 to 48 in the vicinities of the quantitative valves, it is possible to prevent the generation of air pockets and to fill the flow channel with an amount of liquid equal to the volume of the region defined by the quantitative valve, whereby accurate quantification can be realized.

(Discharge Flow Channels)

The discharge flow channels 51 to 56 are provided to discharge the liquid from the first circulation flow channel 10, the second circulation flow channel 20, or the third circulation flow channel 30. The discharge flow channels 51 to 56 are provided with discharge flow channel valves 01 to 06 for opening and closing the discharge flow channels, respectively. Among the discharge flow channels 51 to 56, the discharge flow channel 56 connected to one end of the overlapping shared flow channel 2 functions as a recovery flow channel for collecting the reacted liquid. Therefore, a recovery tank (not shown) is connected to the terminal of the discharge flow channel (recovery flow channel) 56. The other discharge flow channels 51 to 55 are connected to the waste liquid tank 70 or the waste liquid tank 71. The waste liquid tanks 70 and 71 are provided with outlets 70a and 71a which are connected to an external suction pump (not shown) and are opened on the surface of the substrate for negative pressure suction. In addition, in the fluidic device 100 of the present embodiment, the waste liquid tank 70 is disposed in an inside region of the loop flow channel 1, and the waste liquid tank 71 is disposed in an inside region of the first bypass flow channel 6. This makes it possible to reduce the size of the fluidic device 100.

Similar to the introduction flow channels 41 to 48, the discharge flow channels 51 to 56 are arranged near the quantitative valves. This makes it possible to suppress the residual liquid at the time of discharge by disposing the discharge flow channels 51 to 56 in the vicinities of the quantitative valves.

(Air Flow Channels)

The air flow channels 61 to 63 are provided to introduce or discharge air from the first circulation flow channel 10. The air flow channels 61 to 63 are provided with air flow channel valves G1, G2 and G3 for opening and closing the flow channels. Air introduction inlets which are opened on the surface of the substrate 9 are provided at ends of the air flow channels 61 to 63. Among the air flow channels 61 to 63, the air flow channel 63 functions as an air discharge flow channel for sucking air out. The other air flow channels 61 and 62 function as air introduction flow channels for introducing air into the flow channels to push out the liquid in the flow channels.

(Purification Method and Detection Method)

Next, methods of purifying and detecting the sample substance using the fluidic device 100 of the present embodiment will be described. According to this embodiment, the nucleic acid can be purified and detected from a specimen liquid such as blood or the like.

First, the quantitative valves V1, V2, and V3 of the first circulation flow channel 10, the valves V6 and V7 positioned at the ends of the first bypass flow channel 6, and the valves V9 and V10 positioned at the ends of the second bypass flow channel 7 are closed. As a result, the first circulation flow channel 10 is compacted into the first quantitative section A1, the second quantitative section A2, and the third quantitative section A3.

Figure 3:
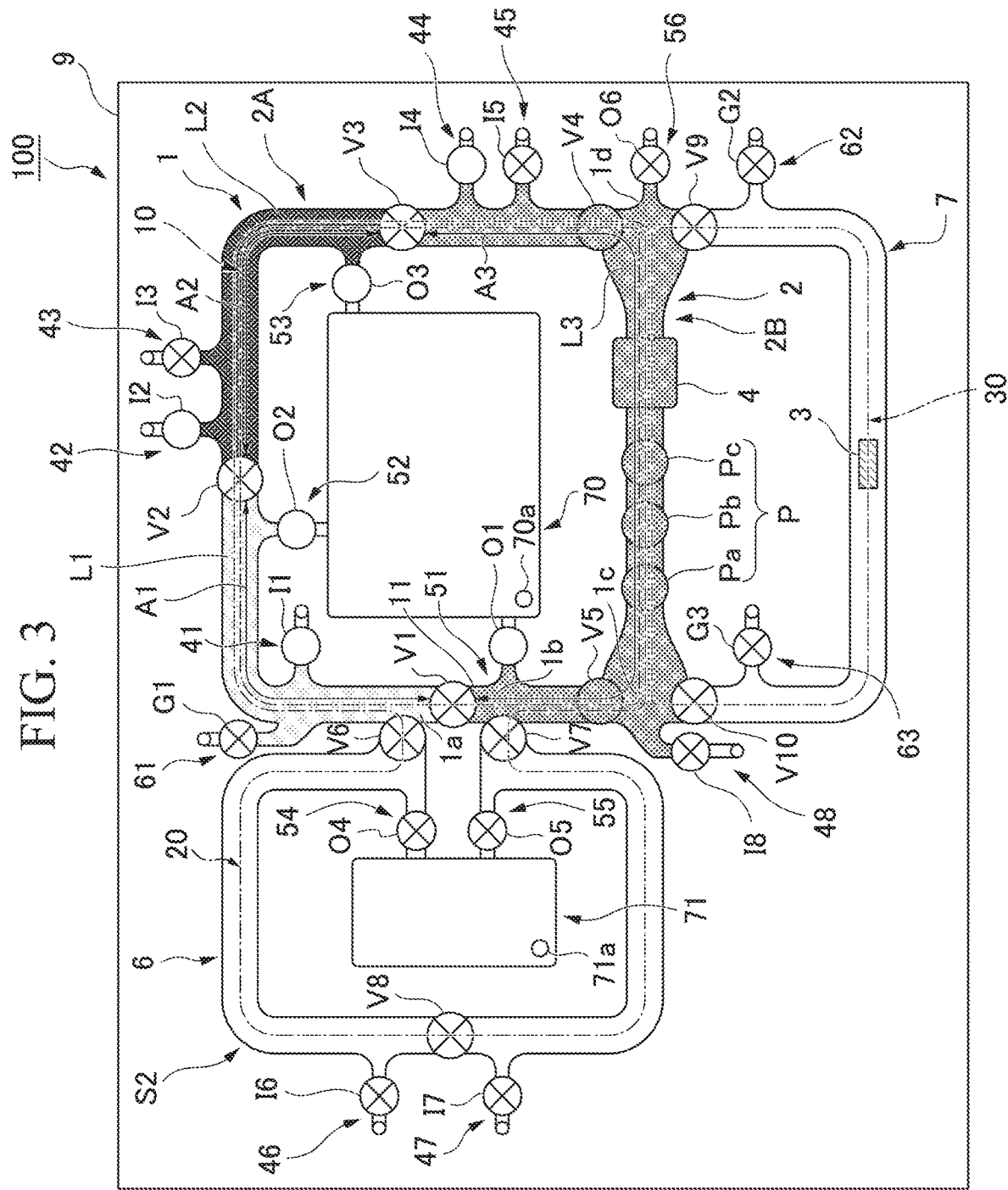
FIG. 3 is a diagram for showing a step of introducing a specimen liquid, a first reagent liquid and a second reagent liquid into the first circulation flow channel in a purification method using the fluidic device of the first embodiment.

Next, as shown in FIG. 3, a specimen liquid (solution) L1 containing a sample substance is introduced from the introduction flow channel 41 into the first quantitative section A1, a first reagent liquid L2 is introduced from the introduction flow channel 42 into the second quantitative section A2, and a second reagent liquid (pretreatment solution) L3 is introduced from the introduction flow channel 44 into the third quantitative section A3. That is, the solution (specimen liquid L1) containing the sample substance, the first reagent liquid L2 and the second reagent liquid L3 are introduced into the circulation flow channel (the first circulation flow channel 10) ahead of the second continuous circulation flow channel S2. Also, the first reagent liquid L2 and the second reagent liquid L3 may be filled beforehand in the second quantitative section A2 and the third quantitative section A3, respectively.

In the present embodiment, the specimen liquid L1 is blood, serum or plasma, and contains nucleic acids as the sample substance.

In the present embodiment, the first reagent liquid L2 is, for example, a solution of proteinase K. Proteinase K inactivates enzymes that degrade nucleic acids (nucleases). Thus, it is possible to suppress the decomposition of the nucleic acid extracted from the specimen liquid L1 by the action of the enzyme.

In the present embodiment, the second reagent liquid L3 is a cell lysis solution for extracting nucleic acid from blood, serum or plasma contained in the specimen liquid L1.

Figure 4:
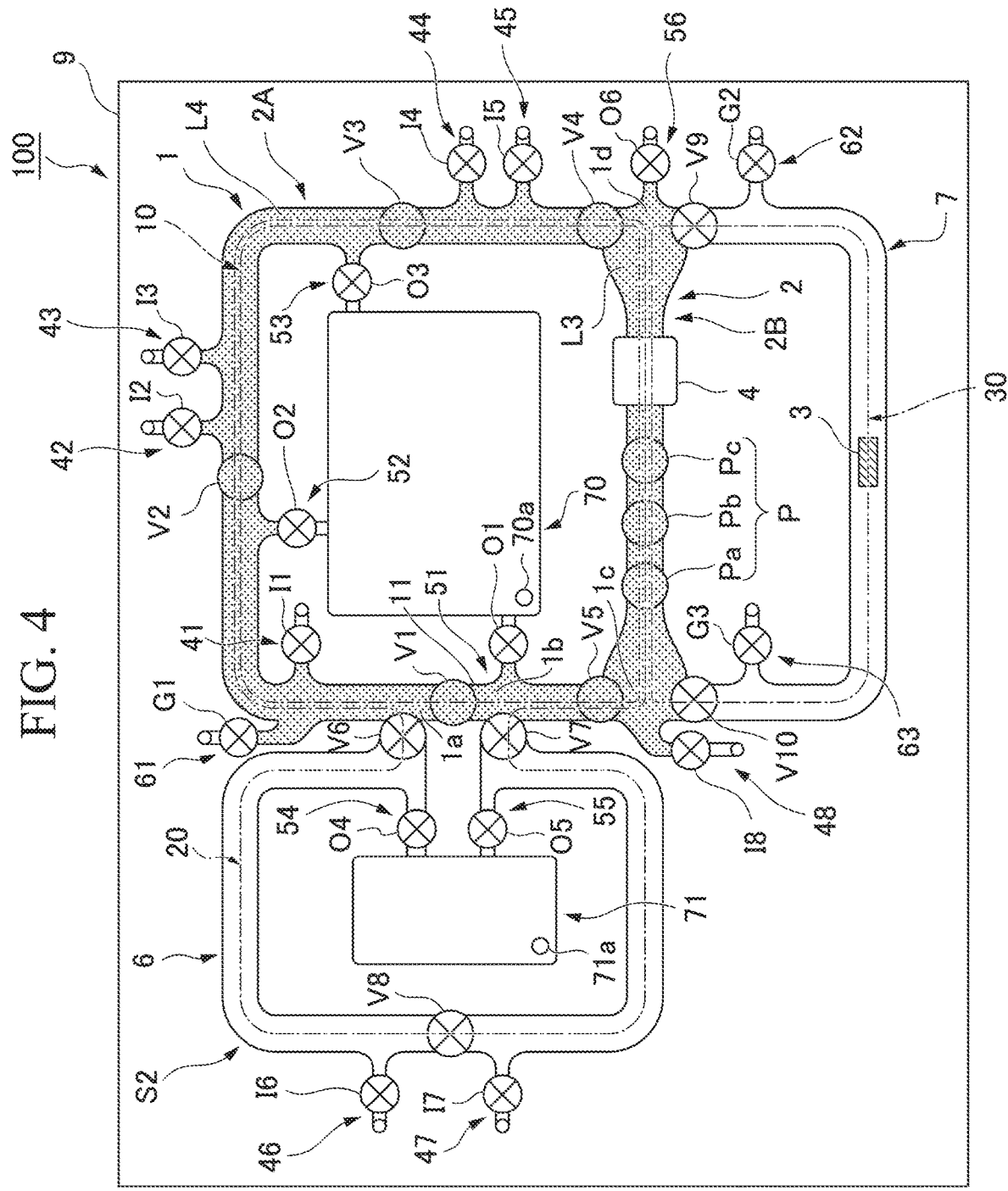
FIG. 4 is a diagram for showing a step of obtaining a first mixed liquid by circulating and mixing the specimen liquid, the first reagent liquid and the second reagent liquid in the first circulation flow channel in the purification method using the fluidic device of the first embodiment.

Next, as shown in FIG. 4, the valves V1, V2, and V3 are opened to make the first circulation flow channel 10 a continuous loop, and then the pump P is driven to circulate and mix the specimen liquid L1, the first reagent liquid L2, and the second reagent liquid L3 in the first circulation flow channel 10, thereby obtaining a first mixed solution L4. By mixing the specimen liquid L1, the first reagent liquid L2 and the second reagent liquid L3, the nucleic acid is extracted as the sample substance.

Figure 5:
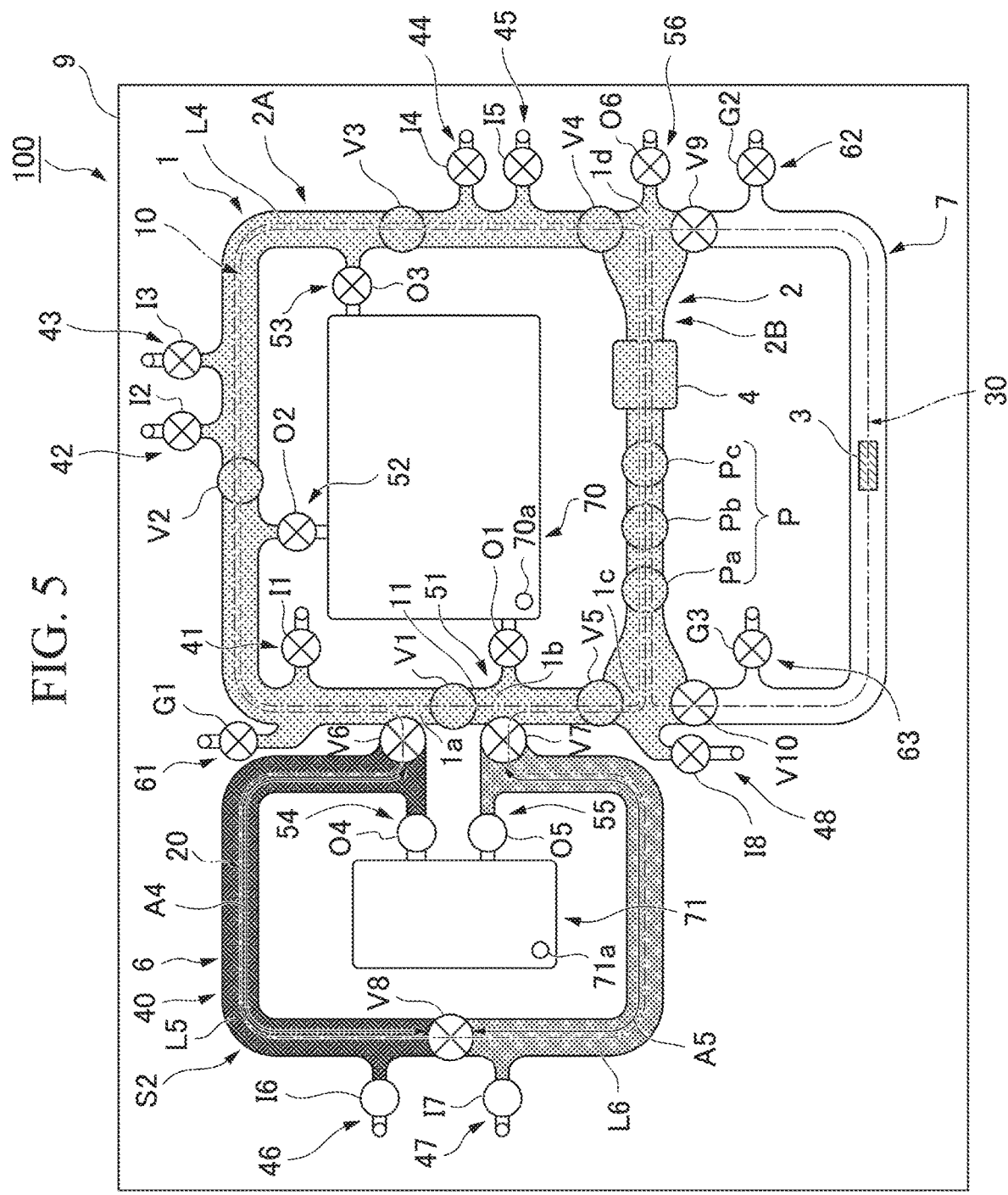
FIG. 5 is a diagram for showing a step of introducing a third reagent liquid and a fourth reagent liquid into a second circulation flow channel in the purification method using the fluidic device of the first embodiment.

Next, as shown in FIG. 5, V6, V7, and V8 in the second circulation flow channel 20 are closed, and the second circulation flow channel 20 is compacted into the fourth quantitative section A4 and the fifth quantitative section A5. Subsequently, a third reagent liquid (solution) L5 containing carrier particles is introduced from the introduction flow channel 46 into the fourth quantitative section A4, and a fourth reagent liquid L6 is introduced from the introduction flow channel 47 into the fifth quantitative section A5. In other words, this step can be referred to as the step of introducing the third reagent liquid L5 and the fourth reagent liquid L6 into the fourth circulation flow channel 40. Also, the third reagent liquid L5 and the fourth reagent liquid L6 may be filled in advance in the fourth quantitative section A4 and the fifth quantitative section A5, respectively.

In the present embodiment, magnetic particles (e.g., silica magnetic particles) are used as the carrier particles contained in the third reagent liquid L5. The silica magnetic particles bind (adsorb) to the nucleic acid (sample substance) in alcohol.

In this embodiment, the fourth reagent liquid L6 is, for example, an isopropanol solution. Isopropanol creates an alcoholic environment to form an environment in which the magnetic particles can bind to the nucleic acid.

Figure 6:
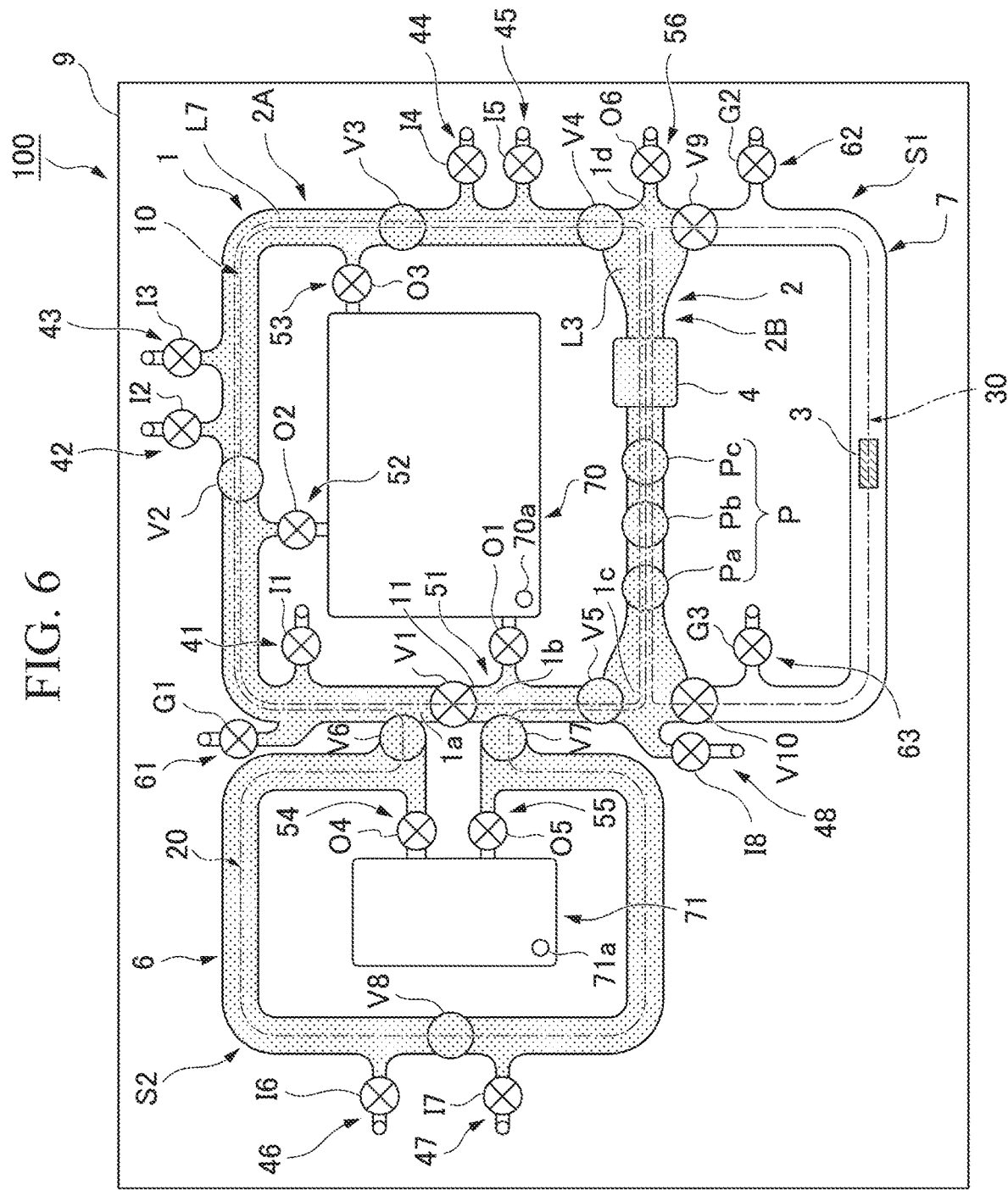
FIG. 6 is a diagram for showing a step of obtaining a second mixed solution by circulating and mixing the first mixed solution, the third reagent liquid and the fourth reagent liquid in the second circulation flow channel in the purification method using the fluidic device of the first embodiment.

Next, as shown in FIG. 6, the valves V6, V7, and V8 are opened and the valve V1 is closed to make the second circulation flow channel 20 a continuous loop, and then the pump P is driven. Thus, the first mixed solution L4 in the first circulation flow channel 10, the third reagent liquid L5, and the fourth reagent liquid L6 are circulated and mixed to obtain a second mixed solution L7. As a result, the magnetic particles (carrier particles) bind to the nucleic acid (sample substance) contained in the first mixed solution L4, and a complex of the sample substance and the carrier particles is produced. In other words, this step can be referred to as a step in which the solutions in both circulation flow channels of the first circulation flow channel 10 and the fourth circulation flow channel 40 (i.e., the second circulation flow channel) in the second continuous circulation flow channel S2 are mixed to obtain a second mixed solution L7.

In addition, after the binding between the nucleic acid and the magnetic particles is sufficiently advanced, a magnet for capturing the magnetic particles in the capturing section 4 is brought close to the flow channel while the second mixed solution L7 is circulated in the second circulation flow channel 20. Thus, the capturing section 4 captures the complex of the sample substance and the carrier particles. The complex of the sample substance and the carrier particles is trapped on an inner wall surface of the flow channel of the capturing section 4.

Next, although this process is omitted from the illustration, the valves V1 and V6 are closed and the valve G1 of the air flow channel 61 is opened to open the valve 04 of the discharge flow channel 54. In addition, by performing a negative pressure suction through the outlet 71a of the waste liquid tank 71, the liquid component (waste liquid) separated from the complex is discharged from the second circulation flow channel to the waste liquid tank 71. Thus, the second mixed solution L7 is removed from the flow channel (overlapping shared flow channel 2) shared by the second continuous circulation flow channel S2 and the third circulation flow channel 30, and the complex of the sample substance and carrier particles captured in the capturing section 4 is separated from the liquid component.

Next, although this process is omitted from the illustration, the valves V6 and V7 are closed to make the first circulation flow channel 10 a continuous loop, and then a cleaning liquid is introduced from the introduction flow channel 43 or the introduction flow channel 45 to fill the first circulation flow channel 10. Also, by driving the pump P, the cleaning liquid is circulated in the first circulation flow channel 10 and cleans the complex of the nucleic acid and magnetic particles captured in the capturing section 4. Further, after the circulation of the cleaning liquid for a predetermined period of time is completed, the cleaning liquid is discharged to the waste liquid tank 70.

In addition, the cycle of introduction, circulation and discharge of the cleaning liquid may be performed multiple times. By repeating the introduction, circulation and discharge of the cleaning liquid, the removal efficiency of unnecessary matters can be increased.

Also, although the present embodiment has illustrated an example in which the cleaning liquid is circulated in the first circulation flow channel 10, the cleaning liquid may be circulated in the second circulation flow channel 20 for cleaning.

Figure 7:
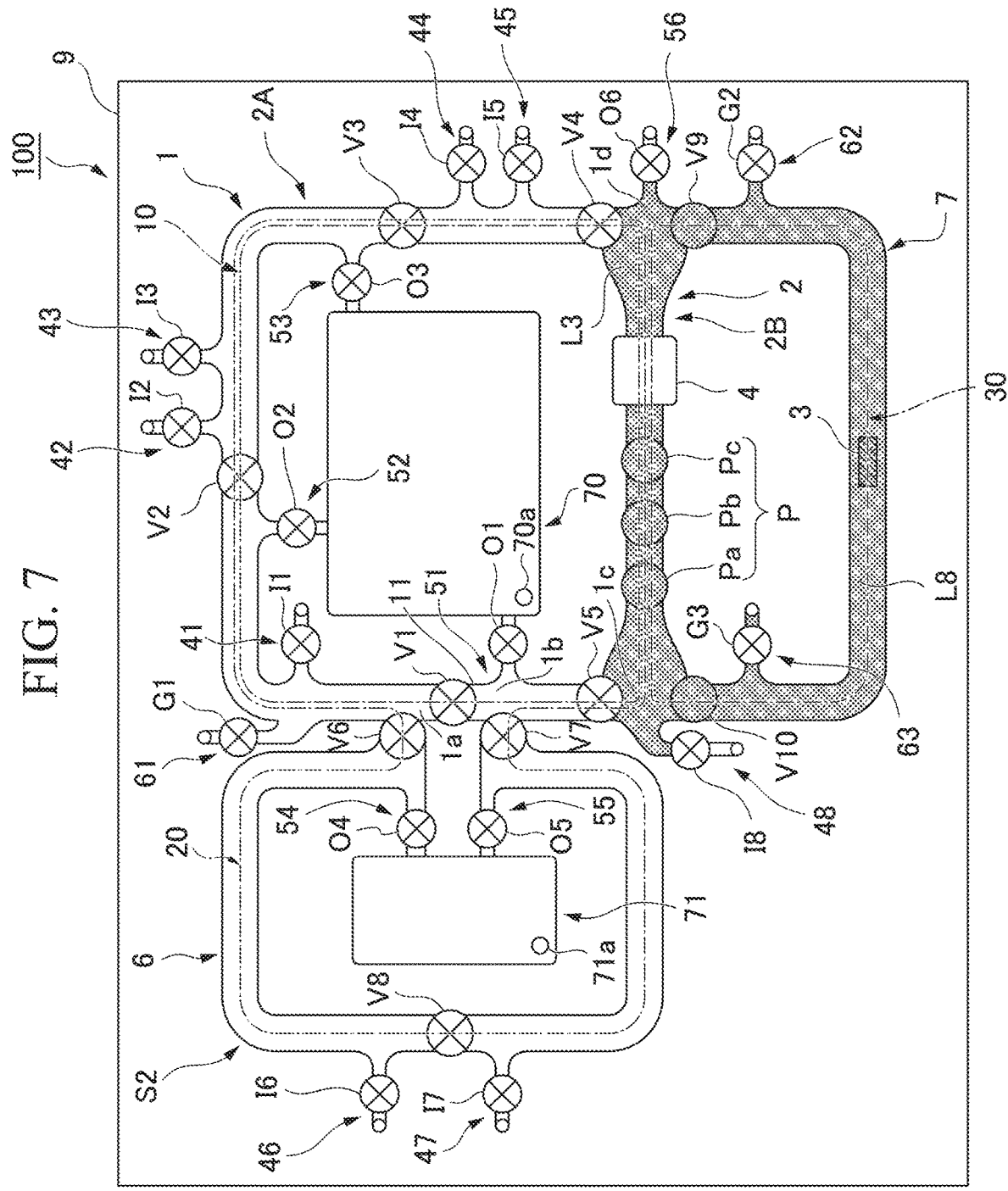
FIG. 7 is a diagram for showing a step of circulating a fifth reagent liquid in the second circulation flow channel in the purification method using the fluidic device of the first embodiment.

Next, as shown in FIG. 7, after the shared flow channel terminal valves V4 and V5 are closed and the shared flow channel terminal valves V9 and V10 are opened to make the third circulation flow channel 30 a continuous loop, a fifth reagent liquid (solution for detection) L8 containing an eluate and a labeling substance (detection assisting substance) is introduced from the introduction flow channel 48 to fill the third circulation flow channel 30 with the fifth reagent liquid L8.

In the present embodiment, the eluate contained in the fifth reagent liquid L8 is, for example, water. As mentioned above, the silica magnetic particles bind to nucleic acids in alcohol, but not in water.

Therefore, by immersing the nucleic acid bound to the magnetic particles in water, the nucleic acid can be eluted from the magnetic particles. In addition, the fifth reagent liquid L8 includes the labeling substance that binds to the nucleic acid (sample substance) and assists with the detection in the detecting section. Also, the fifth reagent liquid L8 may be a solution suitable for storage of nucleic acid.

Next, the fifth reagent liquid L8 is circulated in the third circulation flow channel 30 by driving the pump P with the complex of the nucleic acid and the magnetic particles released or not released in the capturing section 4. Thus, the nucleic acid is eluted from the complex of the nucleic acid and the magnetic particles and the labeling substance binds to the nucleic acid, thereby producing a complex of the sample substance and the labeling substance. When the complex of the nucleic acid and the magnetic particles is released from the capturing section 4 and circulated, capturing is started again by the capturing section 4 as a next step, and the magnetic particles are captured again. In this way, the magnetic particles can be removed from the liquid, leaving only the nucleic acid bound to the labeling substance in the solution.

The nucleic acid can be purified through the above steps. In addition, when pure water not containing the labeling substance is used for the fifth reagent liquid L8, a solution containing only nucleic acid in water can be purified. In this case, the purified solution can be recovered from the discharge flow channel (recovery flow channel) 56.

Next, by detecting the labeling substance in the detecting section 3, the nucleic acid bound to the labeling substance is indirectly detected. When an enzyme is used as the labeling substance, the detection section 3 can detect the nucleic acid by detecting the reaction product such as a dye, fluorescence, or the like created by the reaction with the substrate using the detecting section 3.

By following the procedure described above, it is possible to detect the sample substance using the fluidic device 100.

Also, the flow directions of the solution in the overlapping shared flow channel 2 when the solution is circulated in each of the first to third circulation flow channels 10, 20 and 30 may be identical or opposite to each other. The term "circulate" means not only a case where a fluid flows in one direction but also a case where the fluid reciprocates in a circulation flow channel at a constant cycle.

As shown in FIG. 1, the fluidic device 100 of the present embodiment includes the first continuous circulation flow channel S1 formed with two continuous circulation flow channels (the second circulation flow channel 20 and the third circulation flow channel 30) which share a portion of the flow channels (the second shared flow channel 2B). The first continuous circulation flow channel S1 is configured such that the solution is circulated in the preceding circulation flow channel (the second circulation flow channel 20) and then circulated in the subsequent circulation flow channel (the third circulation flow channel 30). Since the first continuous circulation flow channel S1 has the second shared flow channel 2B in the preceding circulation flow channel and the subsequent circulation flow channel, at least part of the liquid which is circulated and mixed in the preceding circulation flow channel can be circulated in the subsequent circulation flow channel without going through a transferring process. That is, since the transferring process can be omitted, the working efficiency can be increased and the detection can be performed in a short time. In addition, since there is no need for a flow channel for transferring between the second circulation flow channel 20 and the third circulation flow channel 30, a simple structure can be obtained, thereby providing an inexpensive fluidic device 100.

The fluidic device 100 of the present embodiment includes the second continuous circulation flow channel S2 formed with two continuous circulation flow channels (the first circulation flow channel 10 and the fourth circulation flow channel 40). The second continuous circulation flow channel S2 is configured such that the solution is circulated in the preceding circulation flow channel (the first circulation flow channel 10), and then the solutions in both circulation flow channels (the first circulation flow channel 10 and the fourth circulation flow channel 40) can be circulated and mixed. Thus, in addition to the solution mixed in the first circulation flow channel 10, the solution in the fourth circulation flow channel 40 can be further added, circulated, and mixed. Also, the two circulation flow channels form the second circulation flow channel 20.

In the present embodiment, the two continuous circulation flow channels S1 and S2 circulate the solution in the order of the second continuous circulation flow channel S2 and the first continuous circulation flow channel S1. In addition, the subsequent circulation flow channel (the second circulation flow channel 20) of the preceding continuous circulation flow channel (the second continuous circulation flow channel S2) is also used as a preceding circulation flow channel of the subsequent continuous circulation flow channel (the first continuous circulation flow channel S1). As a result, the sample substance is sequentially conveyed into a plurality of three or more circulation flow channels (the first circulation flow channel 10, the second circulation flow channel 20, and the third circulation flow channel 30), so that pretreatment and purification or detection can be carried out continuously in each circulation flow channel.

Since the fluidic device 100 of the present embodiment includes the first continuous circulation flow channel S1 and the second continuous circulation flow channel S2, sequential reactions which require quantitation and mixing of the liquid can be performed sequentially in one device.

In addition, in the present embodiment, the order in which the liquid is circulated in the first continuous circulation flow channel S1 and the second continuous circulation flow channel S2 may be opposite to the order shown in the embodiment. Further, although the present embodiment has illustrated the case where the fluidic device 100 includes a total of two continuous circulation flow channels, i.e., two types of continuous circulation flow channels one by one, it may include three or more, and may further include a flow channel (for example, a straight flow channel) other than the circulation flow channel.

In the present embodiment, the second circulation flow channel 20 and the third circulation flow channel 30 constituting the first continuous circulation flow channel S1 share the capturing section 4 in the second shared flow channel 2B. Therefore, the sample substance to which carrier particles generated by circulation in the second circulation flow channel 20 are bound can be captured in the capturing section 4, and condensed to be carried to the third circulation flow channel 30.

In the present embodiment, the pump P is disposed in the flow channel (that is, the overlapping shared flow channel 2) shared by all of the circulation flow channels of the first continuous circulation flow channel S1 (the first circulation flow channel 10 and the second circulation flow channel 20) and by all of the circulation flow channels (the second circulation flow channel 20 and the third circulation flow channel 30) among the second continuous circulation flow channel S2, in which liquids are circulated. Thus, circulation of the liquids in all the circulation flow channels of the first and second continuous circulation flow channels S1 and S2 can be performed by driving one pump P. That is, according to the present embodiment, it is possible to provide an inexpensive fluidic device 100 with a simple structure by reducing the number of pumps mounted on the fluidic device 100.

In the present embodiment, the first continuous circulation flow channel S1 has the detecting section 3 for detecting the sample substance disposed in the flow channel (the second bypass flow channel 7) that is not shared with the preceding circulation flow channel (the second circulation flow channel 20) in the subsequent circulation flow channel (the third circulation flow channel 30). When pretreatment is performed by mixing the specimen liquid L1 and the first to fourth reagent liquids L2, L3, L5 and L6 in the first continuous circulation flow channel S1, foreign matters unnecessary for detecting the sample substance are generated. This foreign matter may remain on an inner wall of the flow channels and become a background noise for detection. Since the detecting section 3 is provided in the second bypass flow channel 7, it is possible to perform the detection in a flow channel in which no foreign matter remains, thereby reducing the influence of the background noise and improving the detection accuracy.

The fluidic device 100 of the present embodiment has the quantitative valves V1, V2, V3 and V8 provided in the first circulation flow channel 10 and the fourth circulation flow channel 40. This makes it possible to quantify the liquids in the first circulation flow channel 10 and the fourth circulation flow channel 40. Further, according to the present embodiment, since continuous loops can be formed by opening the quantitative valves V1, V2 and V8, it is possible to circulate and efficiently mix the liquids quantified in the circulation flow channels, thereby accelerating the reaction.

In the fluidic device 100 of the present embodiment, any one of the pump valves Pa, Pb and Pc constituting the pump P can be used as a quantitative valve for quantifying the solution. As an example, by closing the pump valve Pa in the third quantitative section A3 of the first circulation flow channel 10, the third quantitative section A3 can be further divided into two sections. In this case, a different solution can be quantified in each of the partitioned sections of the third quantitative section A3. When one of the pump valves Pa, Pb and Pc is used as the quantitative valve, these are provided in the overlapping shared flow channel 2. Accordingly, various compartment areas can be formed with a small number of valves and various quantitative measurements can be performed.

In the fluidic device 100 of the present embodiment, at least one introduction flow channel and discharge flow channel are provided in all of the sections (the first to fifth quantitative sections A1, A2, A3, A4 and A5) of the circulation flow channels partitioned by the quantitative valves. Thus, by performing negative pressure sucking through the discharge flow channel, it is possible to smoothly fill each section with the solution from the introduction flow channel.

[System]

As shown in FIG. 1, a system 91 according to one embodiment of the present invention includes the fluidic device 100 and a control unit 90. The control unit 90 is connected to the valves provided in the fluidic device 100 via a connection line (not shown), and controls opening and closing of the valves. According to the system 91 of the present embodiment, the mixing, capturing and detecting in the fluidic device 100 can be performed.

[Modification of First Embodiment]

Next, modifications applicable to the first embodiment will be described. The present modification is mainly different from the first embodiment in that a second detecting section 3A (the two-dotted chain line in FIG. 1) is additionally provided together with the capturing section 4.

The second detecting section 3A is disposed to overlap the capturing section 4. The second detecting section 3A is provided for detecting a sample substance. In addition, the second detecting section 3A is provided to detect a sample substance which is different from that detected by the detecting section 3 (hereinafter, the first detecting section 3) of the second bypass flow channel 7. The first detecting section 3 is used as a detecting section that detects a sample substance susceptible to background noise. On the other hand, the second detecting section 3A can be preferably used as a detecting section that detects a sample substance that is not easily influenced by background noise.

In the fluidic device of the present modification, similarly to the detection method of the first embodiment, the second mixed solution L7 (FIG. 6) is discharged and the complex of the sample substance and the carrier particles captured by the capturing section 4 is separated from the liquid component. Then, a solution for detecting the sample substance is introduced into the second circulation flow channel 20 and circulated, so that the detection can be carried out in the second detecting section 3A.

Also, in this case, the second detecting section 3A may detect the sample substance in a state in which the sample substance is released from the capturing section 4, and the sample substance may be detected without being released from the capturing section 4.

Second Embodiment

Figure 8:
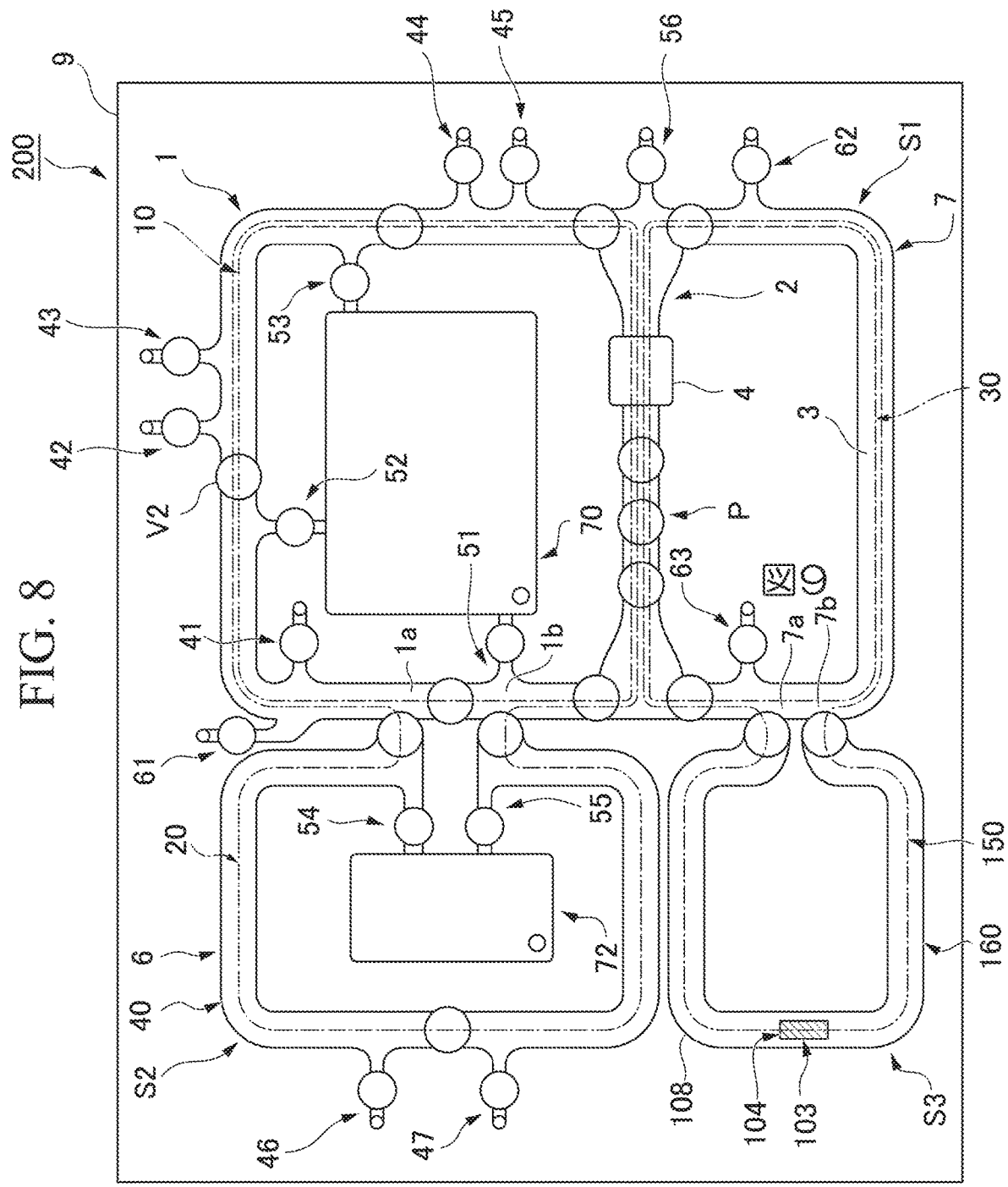
FIG. 8 is a plan view for schematically showing a fluidic device according to a second embodiment.

FIG. 8 is a plan view for schematically showing a fluidic device 200 according to a second embodiment.

The fluidic device 200 of the second embodiment is different from the first embodiment mainly in that it has three continuous circulation flow channels S1, S2 and S3. Also, the same constituent elements as those in the embodiments described above will be denoted by the same reference numerals and the description thereon will be omitted.

The fluidic device 200 of the present embodiment further includes a third bypass flow channel 108 in addition to the loop flow channel 1, the first bypass flow channel 6 and the second bypass flow channel 7. The third bypass flow channel 108 connects and bypasses the pair of connection portions 7a and 7b of the second bypass flow channel 7.

In the flow channel of the third bypass flow channel 108, a second capturing section 104 is provided. The second capturing section 104 also serves as a detecting section 103.

The loop flow channel 1, the first bypass flow channel 6, the second bypass flow channel 7, and the third bypass flow channel 108 form the first circulation flow channel 10, the second circulation flow channel 20, the third circulation flow channel 30, the fourth A circulation flow channel 40, a fifth circulation flow channel 150, and a sixth circulation flow channel 160.

The first to fourth circulation flow channels 10, 20, 30 and 40 have the same configuration as in the first embodiment.

Each of the fifth circulation flow channel 150 and the sixth circulation flow channel 160 includes a portion of the third circulation flow channel 30 and the third bypass flow channel 108. The portion of the third circulation flow channel 30 included in the fifth circulation flow channel 150 and the portion of the third circulation flow channel 30 included in the sixth circulation flow channel 160 are different from each other. The portion of the third circulation flow channel 30 included in the fifth circulation flow channel 150 is one flow channel having a long distance among the two flow channels divided by the pair of connection portions 7a and 7b. On the other hand, the portion of the third circulation flow channel 30 included in the sixth circulation flow channel 160 is one flow channel having a short distance among the two flow channels divided by the pair of connection portions 7a and 7b. The sixth circulation flow channel 160 is mainly used for quantifying a solution. In the present embodiment, the sixth circulation flow channel 160 is not used as a single body for circulating a liquid. However, by arranging valves respectively in the vicinities of the connection portions 7a and 7b in the long flow channel among the two flow channels divided by the connection portions 7a and 7b in the third circulation flow channel 30 and closing these valves, the sixth circulation flow channel 160 may be configured to be used as a single body for circulating the liquid.

The sixth circulation flow channel 160 is provided to circulate a solution in the third circulation flow channel, and then circulate and mix solutions in both circulation flow channels of the third circulation flow channel 30 and the sixth circulation flow channel 160. The third circulation flow channel 30 and the sixth circulation flow channel 160 are connected to each other to form the fifth circulation flow channel 150.

A valve may be disposed between the connection portions 1a and 1b (the short one) in the third circulation flow channel, and the valve may be closed when the liquid is circulated in the fifth circulation flow channel. In this way, it is possible to flow the liquid through the fifth circulation flow channel in one direction.

The second circulation flow channel 20 and the third circulation flow channel 30 constitute the first continuous circulation flow channel S1. The first circulation flow channel 10 and the fourth circulation flow channel 40 constitute the second continuous circulation flow channel S2. The third circulation flow channel 30 and the sixth circulation flow channel 160 constitute a third continuous circulation flow channel (the second type continuous circulation flow channel) S3.

As in the first embodiment, the first continuous circulation flow channel S1 is classified as the first type continuous circulation flow channel, and the second continuous circulation flow channel S2 is classified as the second type continuous circulation flow channel.

The third continuous circulation flow channel S3 is formed with two continuous circulation flow channels (the third circulation flow channel 30 and the sixth circulation flow channel 160). The third continuous circulation flow channel S3 is configured to circulate a solution in the preceding circulation flow channel (the third circulation flow channel 30), and then circulate and mix solutions in both circulation flow channels of the third circulation flow channel 30 and the sixth circulation flow channel 160 (that is, the fifth circulation flow channel 150). Therefore, the third continuous circulation flow channel S3 is classified into the second type continuous circulation flow channel.

The second capturing section 104 of the present embodiment is a DNA microarray. The second capturing section 104 has a nucleic acid probe which is arranged in the flow channel and has a gene sequence that hybridizes complementarily to a sample substance (nucleic acid, particularly RNA in this embodiment).

Figure 9:
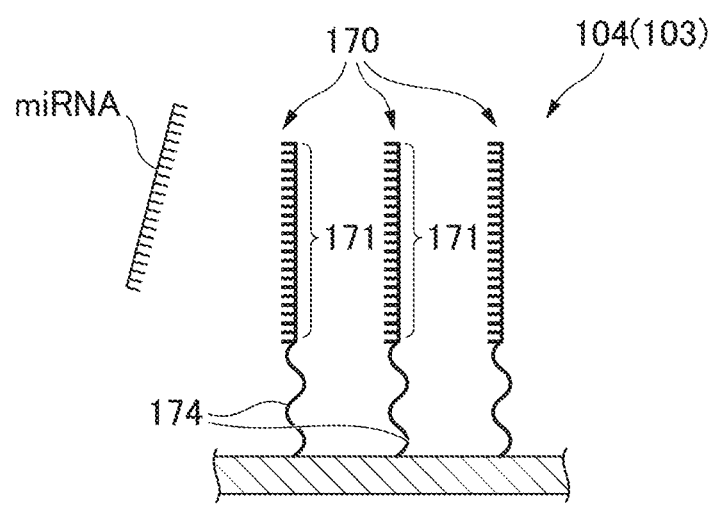
FIG. 9 is a schematic diagram for showing a capturing section used in the fluidic device according to the second embodiment.

FIG. 9 is a schematic diagram of the second capturing section 104. A capturing probe 170 is formed in the second capturing section 104. The capturing probe 170 has a sequence which may hybridize with a nucleic acid to be detected. It should be understood that the term "may hybridize" means that a portion of the capturing probe 170 to be used hybridizes to a target nucleic acid (for example, a target RNA) under stringent conditions, and does not hybridize or is difficult to hybridize to a nucleic acid molecule other than the target nucleic acid. The term "stringent conditions" include, for example, the conditions described in Molecular Cloning-A LABORATORY MANUAL 2nd EDITION (Sambrook et al., Cold Spring Harbor Laboratory Press).

The capturing probe 170 has a first portion 171 and a spacer 174. The first portion 171 consists of a sequence which may hybridize with RNA. The spacer 174 is provided for the first portion 171 to secure molecular freedom for hybridization of RNA. Although the length of the spacer 174 is not particularly limited, for example, it is 3 bases to 50 bases, or 5 bases to 25 bases. Further, the bases used for the spacer 174 can be substituted with a linker such as PEG and the like which has the same length and softness. In this case, the number of bases used for the spacer 174 may be 0 bases.

The capturing probe 170 may be DNA or RNA. As long as it has the same function as DNA or RNA, it is not limited to natural and non-natural, and it may contain artificial nucleic acids such as peptide nucleic acid (PNA), locked nucleic acid (LNA), bridged nucleic acid (BNA), etc. The capturing probe 170 may also include LNA or BNA from the perspective that, compared to DNA and RNA, it has high affinity with the target RNA, is not easily recognized by DNA degrading enzymes and RNA degrading enzymes, and can be a substrate of DNA ligase such as T4 DNA ligase and the like.

In the present embodiment, the second capturing section 104 also serves as the detecting section 103. As a method for quantifying RNA using a DNA microarray, for example, the following method can be employed. First, a detection assisting substance (a labeling substance) for fluorescently labeling is bound to RNA to be detected is bound in advance. After cleaning the RNA hybridized to the second capturing section 104, the RNA amount is estimated using the fluorescence intensity as an index. That is, the detecting section 103 indirectly detects RNA by detecting the detection assisting substance bound to RNA. As the detection assisting substance, a labeling substance for fluorescently labeling RNA can be employed.

(Detection Method)

Next, a method for detecting RNA using the fluidic device 200 of the present embodiment will be described.

First, the nucleic acid is purified by the same procedure as in the first embodiment. That is, in the first circulation flow channel 10, the specimen liquid and the pretreatment solution are circulated and RNA is extracted to obtain the first mixed solution. Next, in the second circulation flow channel 20, the second mixed solution and the solution containing carrier particles are circulated to obtain the second mixed solution containing the complex of RNA and the carrier particles. Further, while circulating the second mixed solution in the second circulation flow channel 20, the complex is captured in the capturing section 4 (hereinafter, the first capturing section 4). Subsequently, by removing the second mixed solution from the overlapping shared flow channel 2, the complex captured by the first capturing section 4 is separated from the liquid component. As a result, the complex remains in the overlapping shared flow channel 2.

Subsequently, while being captured by the first capturing section 4, the cleaning liquid is introduced into the third circulation flow channel 30 and is circulated in the third circulation flow channel 30, so that the complex is washed.

Next, the valves positioned at both ends of the third bypass flow channel 108 are opened to make the fifth circulation flow channel 150 a continuous loop, and the solution for detection containing the eluate and the labeling substance (detection assisting substance) is circulated in the fifth circulation flow channel 150. As a result, while the complex is captured by the first capturing section 4, the nucleic acid is eluted from the complex of the nucleic acid and the magnetic particles and the labeling substance is bound to the nucleic acid, thereby generating the complex of RNA and the labeling substance.

Next, in the second capturing section 104, RNA is hybridized to the capturing probe 170. Subsequently, after RNA nonspecifically absorbed on the substrate is washed, RNA can be detected by observing the second capturing section 104 to estimate the amount of RNA using the fluorescence intensity as an index.

Further, although the detection target is RNA in the present embodiment, other biomolecules (for example, nucleic acids such as DNA, RNA, etc.) can also be detected with the same configuration.

According to the fluidic device 200 of the present embodiment, effects similar to those of the first embodiment can be provided.

Further, in the present embodiment, the three continuous circulation flow channels S1, S2 and S3 are configured to perform circulating through the second continuous circulation flow channel S2, then circulating through the first continuous circulation flow channel S1, and further circulating through the third continuous circulation flow channel S3. That is, the fluidic device 200 includes the second type continuous circulation flow channel, the first type continuous circulation flow channel, and the second type continuous circulation flow channel in this order. In addition, the subsequent circulation flow channel of the preceding continuous circulation flow channel is also used as the preceding circulation flow channel of the subsequent continuous circulation flow channel. As a result, by sequentially conveying the sample substance in four or more plural circulation flow channels (the first circulation flow channel 10, the second circulation flow channel 20, the third circulation flow channel 30, and the fifth circulation flow channel 150), pretreatment and purification or detection can be carried out continuously in each circulation flow channel.

That is, the fluidic device 200 of the present embodiment can sequentially perform more complicated sequential reactions requiring quantitation and mixing of liquids in one device.

While the various embodiments of the present invention have been described above, it should be appreciated that the respective configurations and combinations thereof in the respective embodiments are merely examples, and additions, omissions, substitutions, and other modifications of the configurations are possible without departing from the gist of the present invention. The present invention is not limited by the embodiments as well.

What is claimed is:

1. A fluidic device for capturing or detecting a sample substance contained in a solution, comprising at least two continuous circulation flow channels selected from the group consisting of:
   a first type continuous circulation flow channel which is formed of a first circulation flow channel and a second circulation flow channel and which is configured to circulate the solution in the first circulation flow channel and then circulate the solution in the second circulation flow channel; and
   a second type continuous circulation flow channel which is formed of a third circulation flow channel and a fourth circulation flow channel and which is configured to circulate the solution in the third circulation flow channel and then circulate and mix the solution in both of the third and fourth circulation flow channels,
wherein any one of the circulation flow channels has a capturing section which captures the sample substance, and/or a detecting section which detects the sample substance,
wherein in the second type continuous circulation flow channel,
the third circulation flow channel consists of a shared flow channel that is shared by the fourth circulation flow channel and a non-shared flow channel having a shorter flow channel length than the shared flow channel, and a first valve is provided in the non-shared flow channel,
wherein the second circulation flow channel consists of the shared flow channel and a bypass flow channel that is connected to the shared flow channel at a pair of connecting portions, and
wherein the pair of connecting portions are provided at a position adjacent to the first valve, and each of the pair of connection portions has each of second and third valves.

2. The fluidic device according to claim 1,
wherein in the first type continuous circulation flow channel,
the first circulation flow channel consists of a shared flow channel that is shared by the second circulation flow channel and a non-shared flow channel,
wherein the second circulation flow channel consists of the shared flow channel that is shared by the first circulation flow channel and a bypass flow channel that is connected to the shared flow channel at a pair of connecting portions, and
wherein the pair of connecting portions has a lower surface and an upper surface having a triangle shape, an apex of the triangle is connected to the non-shared flow channel of the first circulation flow channel, a valve that adjusts a flow of a fluid in a flow channel is provided on the apex of the triangle, another apex of the triangle is connected to the bypass flow channel of the second circulation flow channel, and a valve that adjusts a flow of a fluid in a flow channel is provided on the another apex of the triangle.

3. The fluidic device according to claim 1, wherein the second circulation flow channel of the first type continuous circulation flow channel is used as the third circulation flow channel of the second type continuous circulation flow channel, and/or
the fourth circulation flow channel of the second type continuous circulation flow channel is used as the first circulation flow channel of the first type continuous circulation flow channel.

4. The fluidic device according to claim 1,
wherein the first type continuous circulation flow channel is configured such that the first circulation flow channel and the second circulation flow channel share at least a portion of the flow channels, and
the shared flow channel has at least one selected from the group consisting of the capturing section, the detecting section, a valve and a pump.

5. The fluidic device according to claim 1,
wherein the second type continuous circulation flow channel has a capturing section for capturing the sample substance in the fourth circulation flow channel.

6. The fluidic device according to claim 4,
wherein the second type continuous circulation flow channel and the first type continuous circulation flow channel are included in that order, and the fourth circulation flow channel of the second type continuous circulation flow channel is used as the first circulation flow channel of the first type continuous circulation flow channel, and
in the first type continuous circulation flow channel, the first circulation flow channel and the second circulation flow channel share at least a portion of the flow channels, the shared flow channel has the pump and the capturing section, and the detecting section is disposed in a flow channel which is not shared with the first circulation flow channel in the second circulation flow channel.

7. The fluidic device according to claim 1,
wherein the second type continuous circulation flow channel, the first type continuous circulation flow channel and the second type continuous circulation flow channel are included in that order, the fourth circulation flow channel of the former second type continuous circulation flow channel is used as the first circulation flow channel of the first type continuous circulation flow channel, and the second circulation flow channel of the first type continuous circulation flow channel is used as the third circulation flow channel of the latter second type continuous circulation flow channel,
in the first type continuous circulation flow channel, the first circulation flow channel and the second circulation flow channel share at least a portion of the flow channels, and the capturing section is disposed in the shared flow channel, and
in the latter second type continuous circulation flow channel, the capturing section and/or the detecting section are disposed in the fourth circulation flow channel.

8. The fluidic device according to claim 1,
wherein at least one circulation flow channel has two or more quantitative valves, and each of the quantitative valves is arranged such that each of sections of the circulation flow channel partitioned by the quantitative valves has a predetermined volume.

9. The fluidic device according to claim 8,
wherein at least one introduction flow channel and at least one discharge flow channel are connected to all of the sections of the circulation flow channel partitioned by the quantitative valves.

10. The fluidic device according to claim 9,
wherein the introduction flow channel and the discharge flow channel are disposed close to the quantitative valves.

11. The fluidic device according to claim 1,
wherein the capturing section captures the sample substance bound to a carrier particle.

12. The fluidic device according to claim 10,
wherein a magnet capable of controlling magnetic force is capable of being disposed close to the capturing section.

13. A system comprising:
the fluidic device according to claim 1; and
a control unit for controlling opening and closing of a valve.

14. A fluidic device for capturing or detecting a sample substance contained in a solution, comprising:
a first circulation flow channel;
a second circulation flow channel; and
a third circulation flow channel, wherein the first circulation flow channel and the second circulation flow channel share a first shared flow channel,
the first circulation flow channel and the third circulation flow channel share a second shared flow channel,
the first shared flow channel or the second shared flow channel has a capturing section which captures the sample substance, and/or the first shared flow channel or the second shared flow channel has a detecting section which detects the sample substance, and
wherein the first shared flow channel and the second shared flow channel share at least a portion of the flow channels.

15. The fluidic device according to claim 14,
wherein the flow channel shared by the first shared flow channel and the second shared flow channel has at least one selected from the group consisting of the capturing section, the detecting section, a valve, and a pump.

16. A method for detecting a sample substance, comprising:
using a fluidic device including a continuous circulation flow channel which is formed of a first circulation flow channel and a second circulation flow channel and which is configured to circulate a solution in the first circulation flow channel and then circulate and mix solutions in both circulation flow channel of the first circulation flow channel and the second circulation flow channel, and a third circulation flow channel which shares at least a portion of the flow channel with the continuous circulation flow channel and which is configured to circulate the solution after circulating the solution in the continuous circulation flow channel, the fluidic device having a capturing section for capturing a sample substance at the flow channel shared by the continuous circulation flow channel and the third circulation flow channel,
and further comprising the steps of:
introducing a solution containing the sample substance into the first circulation flow channel of the continuous circulation flow channel;
obtaining a first mixed solution by circulating and mixing the solution containing the sample substance and a pretreatment solution in the first circulation flow channel of the continuous circulation flow channel;
obtaining a second mixed solution containing a complex of the sample substance and a carrier particle by circulating the first mixed solution and a solution containing the carrier particle bound to the sample substance in both of the circulation flow channels of the continuous circulation flow channel;
capturing the complex in the capturing section by further circulating the second mixed solution in the continuous circulation flow channel;
removing the second mixed solution from a flow channel shared by the continuous circulation flow channel and the third circulation flow channel; and
detecting the sample substance by circulating a detection solution in the third circulation flow channel while releasing or not releasing the sample substance or the complex from the capturing section.

17. The method for detecting the sample substance according to claim 16,
wherein the sample substance is a nucleic acid,
the solution containing the sample substance is blood, serum, or plasma,
the pretreatment solution is a cell lysis solution,
the carrier particle is a silica magnetic particle, and
the capturing section is capable of disposing a magnet close to the capturing section.

18. A fluidic device comprising,
a first circulation flow channel and a second circulation flow channel that are configured to circulate a solution including a sample substance,
wherein the first circulation flow channel and the second circulation flow channel comprise a shared flow channel which share at least a portion with the first circulation flow channel and the second circulation flow channel,
the first circulation flow channel comprises the shared flow channel and a non-shared flow channel which has a flow channel distance shorter than the shared flow channel and which does not share a flow channel with the second circulation flow channel,
the first circulation flow channel further comprises a first valve in the non-shared flow channel, and
the second circulation flow channel comprises (i) the shared flow channel, (ii) a second valve and a third valve that are disposed in a vicinity of both ends of the first valve, respectively and that are connected to the shared flow channel and (iii) a bypass flow channel that is connected to the shared flow channel via the second valve and the third valve.

19. The fluidic device according to claim 18,
the first circulation flow channel comprises a first loop flow channel to quantify a filled solution which includes two or more types of solutions having different volume with each other, and that is configured to circulate the quantified solution including the two or more types of solutions,
the bypass flow channel of the second circulation flow channel is formed so as to be able to quantify a filled solution and is disposed at a position extended in a first direction with respect to the first loop flow channel,
the device further comprising a third circulation flow channel that is formed of a second loop flow channel which is disposed at a position extended in a direction substantially perpendicular to the first direction,
wherein the second loop flow channel includes,
a shared flow channel which shares a flow channel with a part of the first loop flow channel, and
at least one of a capturing section that captures a sample substance and a detecting section that detects a sample substance, and the third circulation flow channel is configured to circulate a solution after the solution has been circulated in the first circulation flow channel and the second circulation flow channel.

20. The fluidic device according to claim 19,
in the first circulation flow channel, a shared flow channel that shares a flow channel with the second circulation flow channel has a longer flow channel length with respect to a non-shared flow channel, which does not share a flow channel with the second circulation flow channel, in the first circulation flow channel.

* * * * *